United States Patent [19]

Barbaret et al.

[11] Patent Number: Plant 6,287

[45] Date of Patent: Sep. 13, 1988

[54] CARNATION VARIETY 'LONVIATEX'

[75] Inventors: Nicole Barbaret; Yves Ducloux, both of Antibes, France

[73] Assignee: Laboratoire de Physiologie Vegetale de la Londe, La Londe, France

[21] Appl. No.: 890,456

[22] Filed: Jul. 29, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of standard carnations having blossoms of medium size and a generally purple color which are borne singly on strong stems of medium length, and the blooms being produced profusely during the recurrent blooming habit of the plant; the plant itself being a fairly tall bush having a height of about one meter with moderately abundant foliage and a vigorous, upright and rather rigid growth habit.

No Drawings

BACKGROUND OF THE NEW PLANT

This new carnation variety originated as a natural mutation of the variety 'Lonsico' (U.S. Plant Pat. No. 5,446) and was discovered in 1982 in a field of the parent variety grown at La Londe, Les Maures, var. France. Because of the very attractive coloration of this discovery sport, we made several reproductions by means of cuttings with such satisfactory results that we began a program of asexual reproduction of the new plant through several successive generations at La Londe by means of cuttings, which demonstrated to our satisfaction that the novel and distinctive characteristics of the original sport were fully maintained from generation to generation and appeared to be firmly fixed.

DESCRIPTION OF THE DRAWING

This new variety of carnation plant is illustrated by the accompanying photographic drawing which shows, in full color, a bud and several blossoms in various stages of maturity, the colors shown being as nearly true to those specified herein as is reasonably possible to obtain by conventional photographic procedures.

DESCRIPTION OF THE NEW PLANT

The following is a detailed description of our new carnation plant based upon observation of greenhouse grown plants made at La Londe, Les Maures, France, early in 1986, the color designations being according to the R.H.S. Colour Chart published by the The Royal Horticultural Society of London, England.

THE PLANT

Origin: Natural mutation.

Parentage: Carnation variety 'Lonsico' (U.S. Plant Pat. No. 5,446).

Classification:

*Botanic.*—*Dianthus caryophyllus.*

*Commercial.*—Standard carnation.

Form: Tall bush comprising at least four stems emitted from the main stem near the ground.

Height: Approximately one meter at eight months.

Main stem:

*Length.*—Less than 15 cm. due to pinching.

Growth: Vigorous, upright and rather rigid.

Foliage:

*Quantity.*—Moderately abundant.

*Number of leaves.*—More than 120.

*Leaf size.*—Averaging about 13 cm. long and about 1.1 cm. wide at the seventh node.

*Leaf shape.*—Linear with curved margins and acuminate tip.

*Texture.*—Leathery.

*Color.*—Upper side — 189A-B. Under side — 189A-B.

*Ribs and veins.*—Hardly noticeable.

*Rachis.*—Hardly noticeable.

THE BUD

Form: Ovoid.

Size:

*Diameter.*—About 2.3 cm., in average.

*Length.*—About 2.8 cm., in average.

Rate of opening: About normal for carnations.

Color of petals:

*When sepals first divide.*—74C-D with margins of 73D.

*When petals begin to unfurl.*—74B to 74D with 73D at the edges.

Sepals:

*Number.*—Five.

*Shape.*—Joined at the lower part and of ovate character in the upper part withan acuminate apex.

*Character.*—The sepals are hooded over the bud before dividing and when the flowers open, the sepals stand up.

*Color.*—Inside — 145D. Outside — 143D and 144C.

*Striae.*—Longitudinal.

Calyx:

*Shape.*—Columnar.

*Size.*—Medium.

*Splitting.*—The calyx rarely splits.

*Aspect.*—Smooth.

Flower stem:

*Length.*—Averages about 61 cm.

*Character.*—Erect and rather rigid.

*Color.*—189A/B.

THE FLOWER

Blooming habit: Recurrent and profusely during the midseason of spring and fall with a tendency to give fewer blooms in fall.

Size of bloom: Medium.

*Diameter.*—Averaging about 8.5 cm.

*Depth.*—Averaging about 6 cm.

Borne: Singly.

Shape:

*When bloom first opens.*—High centered.

*When bloom matures.*—Ball shaped.

Petalage:

*Number of petals.*—Average about 61.

*Arrangement.*—Imbricated.

*Form.*—Semi-circular with finely serrated apex edges.

*Texture.*—Leathery.

*Appearance.*—Satiny.

*Color.*—Both outer and inner petals: Body — Cyclamen Purple, 74B to 74D, with Mallow Purple, 73D, on the margins. Base — Greenish. Reverse side — 74C and 74D.

Petaloids: Less than ten.

*Size.*—Smaller than the petals.

*Color.*—Same as the petals.

Flower stem: Cut at tenth node, the length averages about 61 cm.

*Character.*—Upright and of good strength.

*Color.*—189A, 189B.

Fragrance: Strong.

Persistence: The petals hang on and dry.

Disease resistance: Rather tolerant to *Fusarium oxysporum* as observed I.N.R.A. Antibes, France.

Lasting quality:

*As a cut flower.*—At least ten days in vase keeping.

REPRODUCTIVE ORGANS

Stamens:

*Number.*—3 to 5 arranged around the ovary.

*Anthers.*—Size: About 4 mm. Color: Greenish white.

*Filaments.*—Length: About 3 cm., in average. Color: Greenish white.

Pistils:

*Number.*—Two.

*Styles.*—Length: About 1.8 cm., in average. Color: Whitish.

*Stigmas.*—Color: Whitish.

Charcter of ovary: The ovary is ribbed.

Compared with the parent 'Lonsico', this sport has a shading off of the violet coloring making it a very attractive flower.

We claim:

1. A new and distinctive carnation cultivar, substantially as herein shown and described, characterized by the relatively light shading of the purple coloring in the body of the petal and the petal margins as compared to the parent plant of which the present plant is a natural mutation.

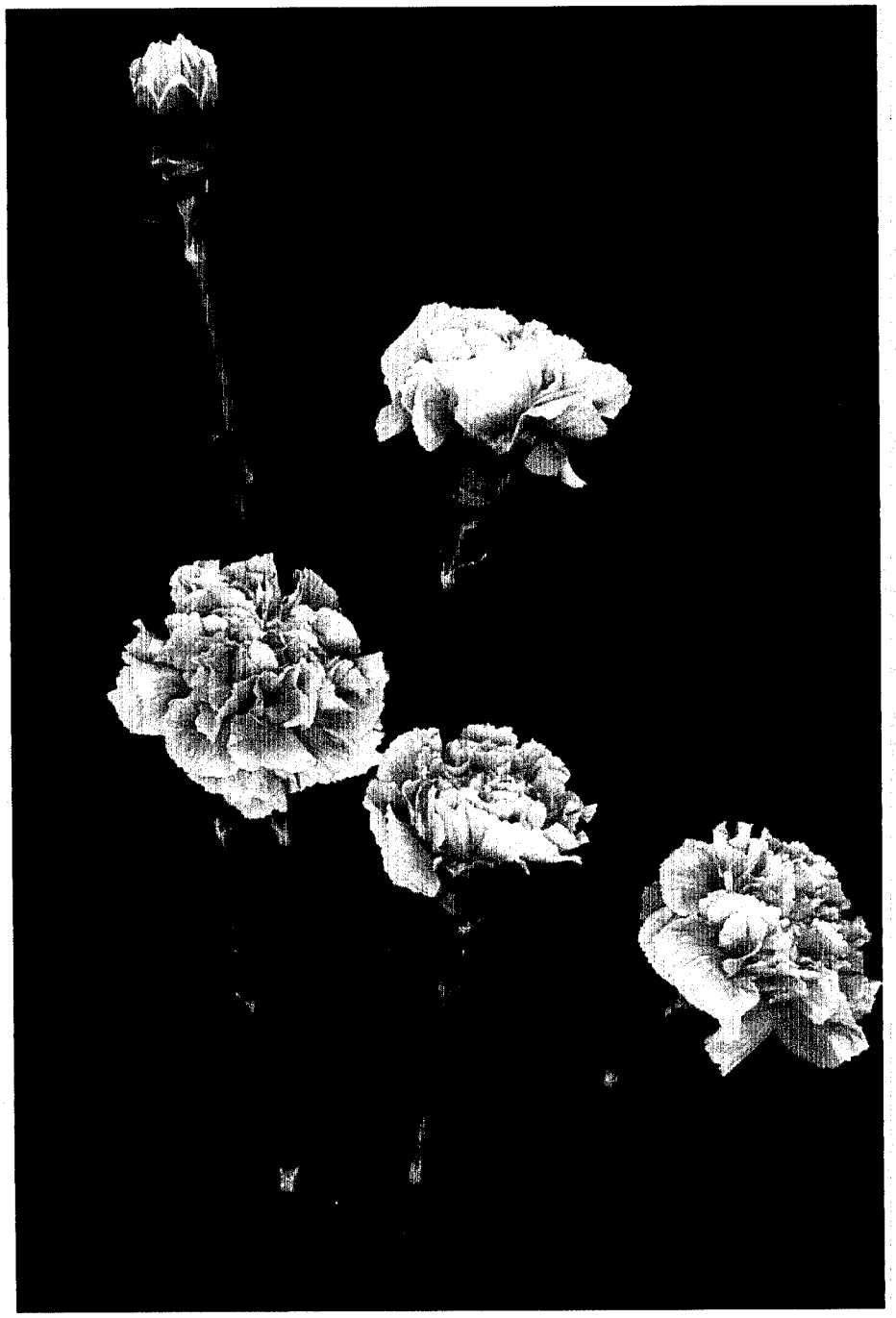

* * * * *